(12) United States Patent
Surbled et al.

(10) Patent No.: US 6,573,235 B1
(45) Date of Patent: Jun. 3, 2003

(54) USE OF HYDROFLUOROETHERS AS AGENTS FOR DISSOLVING AROMATIC COMPOUNDS TO MAKE COMPOSITIONS

(75) Inventors: Michel Surbled, Saint-Nolff (FR); Benoit Lemaire, Sarzeau (FR); Philippe Mengal, Josselin (FR); Bernard Mompon, Vannes (FR)

(73) Assignee: Extractive, Vannes Cedex (FR)

( * ) Notice: Subject to any disclaimer, the term of this patent is extended or adjusted under 35 U.S.C. 154(b) by 0 days.

(21) Appl. No.: 09/554,703

(22) PCT Filed: Nov. 26, 1998

(86) PCT No.: PCT/FR98/02544

§ 371 (c)(1),
(2), (4) Date: Jul. 17, 2000

(87) PCT Pub. No.: WO99/26600

PCT Pub. Date: Jun. 3, 1999

(30) Foreign Application Priority Data

Nov. 26, 1997 (FR) ............................................. 97 15119

(51) Int. Cl.⁷ .................................................. A61K 7/46
(52) U.S. Cl. ............................ 512/1; 512/20; 424/76.4; 252/364
(58) Field of Search ...................... 512/20; 424/76.4; 252/364

(56) References Cited

U.S. PATENT DOCUMENTS

| | | | | |
|---|---|---|---|---|
| 5,571,858 A | | 11/1996 | de La Poterie et al. | |
| 5,741,499 A | * | 4/1998 | Arnauld et al. | 424/401 |
| 6,045,588 A | * | 4/2000 | Estes et al. | 8/137 |
| 6,224,851 B1 | * | 5/2001 | Bara | 424/59 |
| 6,238,651 B1 | * | 5/2001 | Bara | 424/61 |
| 6,251,375 B1 | * | 6/2001 | Bara | 424/61 |

FOREIGN PATENT DOCUMENTS

| | | | |
|---|---|---|---|
| EP | 360 292 | | 3/1990 |
| EP | 296 661 | | 12/1999 |
| EP | 1 029 527 | * | 8/2000 |

* cited by examiner

*Primary Examiner*—Jill Warden
*Assistant Examiner*—Monique T. Cole
(74) *Attorney, Agent, or Firm*—Merchant & Gould P.C.

(57) ABSTRACT

The invention concerns a cosmetic composition comprising at least an aromatic compound and at least an agent for dissolving said aromatic compound, characterized in that said dissolving agent consists of perfluorinated hydrofluoroether preferably having a total number of carbon atoms not less than 5 and consisting of a perfluoroalkane chain, branched or not, cyclized or not, bound to an alkoxy group, said alkoxy group having a number of atom(s) between 1 and 7, said hydrofluoroether having a boiling point in atmospheric pressure ranging between +15° C. and +100° C. The invention enables the replacement of ethanol conventionally used in cosmetic compositions by at least one hydrofluoroether compound.

8 Claims, No Drawings

USE OF HYDROFLUOROETHERS AS AGENTS FOR DISSOLVING AROMATIC COMPOUNDS TO MAKE COMPOSITIONS

The invention relates to the field of the cosmetic industry.

Perfumes, after-shave products, toilet waters, deodorants and, in a general way, all perfumed cosmetic compositions are, for the most part, made up of an ethanolic solution of some titer, most often 90°, containing aromatic preparations which have been refined to a greater or lesser degree.

Ethanol is traditionally used in cosmetics' compositions as a dissolving agent since it offers numerous advantages. It is liquid under normal conditions of pressure and temperature. It permits the dissolution of natural or synthetic aromatic compositions. It does not interact or does so only very slightly with the dissolved molecules. It evaporates rapidly on contact with the skin.

Furthermore, ethanol is a solvent with very low toxicity with respect to the quantities used under normal usage of such cosmetic compositions.

To the knowledge of the applicant, at the present time, other solvents do not exist which could substitute for ethanol in such compositions.

Within the context of cosmetic compositions, the use of ethanol nevertheless does have a certain number of disadvantages.

Since the use of ethanol is prohibited in certain countries, notably Moslem countries, the use of perfumed compositions containing it is also prohibited.

Another disadvantage of ethanol stems from the stinging sensation associated with its use.

Finally, it should be noted that ethanol can also cause drying of the skin and the appearance of red blotches.

The main objective of this invention is to propose a range of compounds capable of being used as dissolving agents in cosmetic compositions, replacing the ethanol.

This objective is achieved thanks to the invention which relates to a cosmetic composition comprising at least one aromatic compound and at least one dissolving agent for said aromatic compound characterized in that said dissolving agent is a perfluorinated hydrofluoro ether.

Therefore the invention proposes to replace ethanol by a perfluorinated hydrofluoro ether in the cosmetic compositions.

Such fluorinated solvents offer crucial advantages when compared with ethanol.

In the first place, perfluorinated hydrofluoro ethers are non-toxic and cause neither red blotches nor any stinging sensation.

Furthermore, the use of hydrofluoro ethers is not subject to any regulation.

In addition, these fluorinated solvents are of interest because they are chemically inert and are not able to react with any of the usual constituents of cosmetic formulations. They are volatile compounds which, after evaporation leave no trace whatsoever.

These fluorinated solvents are also of interest in not being subject to any regulation whatsoever and can therefore be universally used.

The fluorinated compounds proposed by the invention are, in addition, without odor or color. They can therefore be integrated into cosmetic formulations without the risk of masking the perfumes or harming the fragrance of the product or modifying its appearance.

In addition, the hydrofluoro ethers have a lower boiling point than ethanol and above all, very low heat capacity and latent heat of vaporization which permits rapid evaporation without trace. These physical and chemical properties increase the feeling of freshness felt when the perfumed composition is applied.

Finally they present no risk for the ecosystem and conform to the most strict environmental regulations (potential for destroying the ozone layer "ODP" zero and contribution to the greenhouse effect "GWP" very slight).

It should also be noted that the fluorinated solvents proposed by the invention are safer than ethanol since they are non-inflammable and do not have a flash point.

According to a preferred variant, said hydrofluoro ether has a total number of carbon atoms that is greater than or equal to 5 and is made up of a perfluoro alkane chain, branched or not, cyclized or not and aromatic or not, bound to an alkoxy group, said alkoxy group having between 1 and 7 carbon atoms, said hydrofluoro ether having a boiling point at atmospheric pressure of between +15° C. and +100° C.

Also, preferably, said alkoxy group of said fluoro ether has between 1 and 5 carbon atoms.

Advantageously, said hydrofluoro ether has a boiling point at atmospheric pressure of between +30° C. and +80° C.

In the most preferred way, said hydrofluoro ether is chosen from the group made up of methoxy-nonafluorobutane ($C_4F_9OCH_3$) and its isomer $((CF_3)_2CFCF_2OCH_3)$, ethoxy-nonafluorobutane ($C_4F_9OC_2H_5$) and its isomer $((CF_3)_2CFCF_2OC_2H_5)$, and propoxy-undecafluoropentane ($C_5F_{11}OC_3H_7$).

It should also be noted that the composition according to the invention may include at least one co-solvent, preferably chosen from the group made up of ethanol and water. By co-solvent, one understands any molecule of such a chemical nature that may be added in variable quantity to the hydrofluoro ethers for the purpose of modifying the properties of the composition thereby obtained.

Advantageously, said aromatic compound incorporated into the composition according to the invention is chosen from the groups made up of the essential oils, natural and synthetic fragrances and the resin oils.

According to the invention, the natural or synthetic aromatic compounds can be simply diluted in the hydrofluoro ether or hydrofluoro ethers. The proportions of one or other of the constituents is not important since the hydrofluoro ethers have a high solvent power, associated with their ether group, that allows complete dissolution of aromatic compositions.

The invention will be more easily understood from the description which follows of two non-limitative examples of embodiments of the invention.

EXAMPLE 1

An essential oil of lavender grosso (abbreviated to HELG) is incorporated with 100 grams of methoxy nonafluorobutane (abbreviated to MNFB) by successive addition of 15 grams. After each addition one observes the appearance or not of a second phase, which would be a consequence of the insolubility of the essential oil in the MNFB. The table below records these observations for the three temperatures tested 0° C., 25° C. and 50° C.

| No. of HELG additions | Quantity of HELG in the MNFB | Observations at the following solution temperature | | |
|---|---|---|---|---|
| | | 0° C. | 25° C. | 50° C. |
| 1 | 15 g | miscible | miscible | miscible |
| 2 | 30 g | miscible | miscible | miscible |
| 3 | 45 g | miscible | miscible | miscible |
| 4 | 60 g | miscible | miscible | miscible |
| 5 | 75 g | miscible | miscible | miscible |
| 6 | 90 g | miscible | miscible | miscible |
| 7 | 105 g | miscible | miscible | miscible |

The results given in this table show that the essential oil of lavender grosso is miscible in all proportions at and above a temperature of 0° C. in methoxy nonafluorobutane.

EXAMPLE 2

A perfumed composition is prepared by dissolving 10 of essential oil of lavender grosso in 100 grams of methoxy nonafluorobutane (10% solution).

This composition is in the form of a clear, slightly amber colored solution.

20 ml of this solution was sprayed onto the skin. A few seconds were sufficient for complete evaporation of methoxy nonafluorobutane. The skin had the aromatic notes characteristic of the lavender flower.

EXAMPLE 3

An essential oil of lavender grosso (abbreviated to HELG) is incorporated with 100 grams of ethoxy nonafluorobutane (abbreviated to ENFB) by successive additions of 15 grams. After each addition one observes the appearance or not of a second phase, which would be a consequence of the insolubility of the essential oil in the ENFB. The table below records these observations for the three temperatures tested 0° C., 25° C. and 50° C.

| No. of HELG additions | Quantity of HELG in the ENFB | Observations at the following solution temperature | | |
|---|---|---|---|---|
| | | 0° C. | 25° C. | 50° C. |
| 1 | 15 g | miscible | miscible | miscible |
| 2 | 30 g | miscible | miscible | miscible |
| 3 | 45 g | miscible | miscible | miscible |
| 4 | 60 g | miscible | miscible | miscible |
| 5 | 75 g | miscible | miscible | miscible |
| 6 | 90 g | miscible | miscible | miscible |
| 7 | 105 g | miscible | miscible | miscible |

The results given in this table show that the essential oil of lavender grosso is miscible in all proportions at and above a temperature of 0° C. in the ethoxy nonafluorobutane.

EXAMPLE 4

A perfumed composition is prepared by dissolving 10 grams of essential oil of lavender grosso in 100 grams of ethoxy nonafluorobutane (10% solution).

This composition is in the form of a clear, slightly amber colored solution.

20 ml of this solution was sprayed onto the skin. A few seconds was sufficient for complete evaporation of ethoxy nonafluorobutane. The skin had the aromatic notes characteristic of the lavender flower.

EXAMPLE 5

An essential oil of peppermint (abbreviated to HEMP) is incorporated with 100 grams of ethoxy nonafluorobutane (abbreviated to ENFB) by successive additions of 15 grams. After each addition one observes the appearance or not of a second phase, which would be a consequence of the insolubility of the essential oil in the ENFB. The table below records these observations for the two temperatures tested 12° C. and 50° C.

| No. of HEMP additions | Quantity of HEMP in ENFB | Observations at the following solution temperature | |
|---|---|---|---|
| | | 12° C. | 50° C. |
| 1 | 15 g | miscible | miscible |
| 2 | 30 g | miscible | miscible |
| 3 | 45 g | miscible | miscible |
| 4 | 60 g | miscible | miscible |
| 5 | 75 g | miscible | miscible |
| 6 | 90 g | miscible | miscible |
| 7 | 105 g | miscible | miscible |

The results given in this table show that the essential oil of peppermint is miscible in all proportions at and above a temperature of 12° C. in the ethoxy nonafluorobutane.

EXAMPLE 6

A perfumed composition is prepared by dissolving 10 grams of essential oil of peppermint in 100 grams of ethoxy nonafluorobutane (10% solution). This composition is in the form of a clear, translucent solution.

20 ml of this solution was sprayed onto the skin. A few seconds was sufficient for complete evaporation of ethoxy nonafluorobutane. The skin had the aromatic notes characteristic of peppermint.

EXAMPLE 7

An essential oil of sweet orange (abbreviated to HEOD) is incorporated with 100 grams of ethoxy nonafluorobutane (abbreviated to ENFB) by successive additions of 15 grams. After each addition one observes the appearance or not of a second phase, which would be a consequence of the insolubility of the essential oil in ENFB. The table below records these observations for the two temperatures tested 12° C. and 50° C.

| No. of HEOD additions | Quantity of HEOD in ENFB | Observations at the following solution temperature | |
|---|---|---|---|
| | | 12° C. | 50° C. |
| 1 | 15 g | miscible | miscible |
| 2 | 30 g | miscible | miscible |
| 3 | 45 g | miscible | miscible |
| 4 | 60 g | miscible | miscible |
| 5 | 75 g | miscible | miscible |
| 6 | 90 g | miscible | miscible |
| 7 | 105 g | miscible | miscible |

The results given in this table show that the essential oil of sweet orange is miscible in all proportions in ethoxy nonafluorobutane at and above a temperature of 12° C.

EXAMPLE 8

A perfumed composition is prepared by dissolving 10 grams of essential oil of sweet orange in 100 grams of ethoxy nonafluorobutane (10% solution).

This composition is in the form of a clear, slightly amber colored solution.

20 ml of this solution was sprayed onto the skin. A few seconds were sufficient for complete evaporation of ethoxy nonafluorobutane. The skin had the aromatic notes characteristic of lavender flower.

The descriptions of examples of the invention given above do not have the objective of restricting the scope of the invention.

What is claimed is:

1. A composition comprising:
   at least one aromatic compound; and
   at least one agent for dissolving said aromatic compound wherein said dissolving agent consists of a hydrofluoro ether wherein said hydrofluoro ether has a total number of carbons equal to or greater than 5 and wherein said hydrofluoro ether is selected from the group consisting of a linear perfluoroalkane chain, a branched perfluoroalkane chain, a cyclized perfluoroalkane chain, an aromatic perfluoroalkane chain, and mixtures thereof, and wherein said perfluoroalkane chain is bound to an alkoxy group having between 1 and 7 carbon atoms, wherein said composition is used as a cosmetic composition.

2. The composition according to claim 1, wherein said hydrofluoro ether has a boiling point at atmospheric pressure of between +15° C. and +100° C.

3. The composition according to claim 2, wherein said alkoxy group of said hydrofluoro ether has between 1 and 5 carbon atoms.

4. The composition according to claim 2, wherein said hydrofluoro ether has a boiling point at atmospheric pressure of between +30° C. and +80° C.

5. The composition according to claim 3, wherein said hydrofluoro ether is chosen from the group consisting of methoxy-nonafluorobutane ($C_4F_9OCH_3$), its isomer (($CF_3$)$CFCF_2OCH_3$), ethoxy-nonafluorobutane ($C_4F_9OC_2H_5$), its isomer (($CF_3)_2CFCF_2OC_2H_5$), and propoxy-undecafluoropentane ($C_5F_{11}OC_3H_7$).

6. The composition according to claim 1, wherein it includes at least one co-solvent.

7. The composition according to claim 6, wherein said co-solvent is chosen from the group consisting of ethanol and water.

8. The composition according to claim 1, wherein said aromatic compound is chosen from the group consisting of the essential oils, natural or synthetic fragrances and resins oils.

* * * * *